United States Patent [19]

Boschelli et al.

[11] Patent Number: 5,208,253

[45] Date of Patent: May 4, 1993

[54] 3-ALKYLOXY-, ARYLOXY-, OR ARYLALKYLOXY-BENZO(B) THIOPHENE-2-CARBOXAMIDES AS INHIBITORS OF CELL ADHESION

[75] Inventors: Diane H. Boschelli, Plymouth; David T. Connor; Clifford D. Wright, both of Ann Arbor, all of Mich.

[73] Assignee: Warner-Lambert Company, Morris Plains, N.J.

[21] Appl. No.: 840,361

[22] Filed: Feb. 24, 1992

[51] Int. Cl.$^5$ .................... A61K 31/38; C07D 333/56
[52] U.S. Cl. .................... 514/443; 549/52; 549/53; 549/54; 549/55; 549/56
[58] Field of Search .................... 549/52, 53, 54, 55, 549/56; 514/413

[56] References Cited

U.S. PATENT DOCUMENTS

| 4,703,053 | 10/1987 | Connor et al. | 548/254 |
| 4,761,424 | 8/1988 | Carethers et al. | 549/54 |
| 4,800,211 | 1/1989 | Tischler et al. | 514/443 |

OTHER PUBLICATIONS

A Wardlaw, *Clinical and Experimental Allergy*, vol. 20, pp. 619–626 (1990).
C. Smith et al., *J. Clin. Invest.*, vol. 82, 1746–1756 (1988).
J. Pober et al., *The Journal of Immunology*, vol. 137, No. 6, 1893–1896 (1986).
B. Hakkert et al., *Blood*, vol. 78, No. 10, 2721–2726 (1991).
T. Springer, *Nature*, vol. 346, pp. 425–434 (1990).
R. McEver, *Thrombosis and Haemostasis*, vol. 65, (3), 223–228 (1991).
M. Jutila et al., *Transplantation*, vol. 48, No. 5, 727–731 (1989).
M. Valase et al., *Biochemical Pharmacology*, vol. 40, No. 8, 1683–1687 (1990). M. Bevilacgua et al., *Proc. Natl. Acad. Sci.*, vol. 84, 9238–9242 (1987).

*Primary Examiner*—Allen J. Robinson
*Assistant Examiner*—Mark W. Russell
*Attorney, Agent, or Firm*—Ronald A. Daignault

[57] ABSTRACT

3-Alkyloxy-, aryloxy-, or arylalkyloxy-benzo[b]thiophene-2-carboxamides are described as agents which block leukocyte adherence to vascular endothelium and, as such, are effective therapeutic agents for treating inflammatory diseases. Certain of these compounds are novel and methods of preparation are also described.

2 Claims, No Drawings

3-ALKYLOXY-, ARYLOXY-, OR ARYLALKYLOXY-BENZO(B) THIOPHENE-2-CARBOXAMIDES AS INHIBITORS OF CELL ADHESION

BACKGROUND OF THE INVENTION

The present invention is for the use of certain 3- alkyloxy-, aryloxy-, or arylalkyloxy-benzo[b]thiophene-2-carboxamides, and pharmaceutically acceptable salts thereof, to prevent the adhesion of leukocytes to endothelial cells. Leukocyte adherence to vascular endothelium is integral to the pathogenesis of inflammation. The adhesion process precedes transendothelial migration of leukocytes into surrounding tissue and ensuing tissue damage. Compounds that can block this initial adhesive interaction are expected to have efficacy in the treatment of inflammatory diseases such as rheumatoid arthritis, asthma, and psoriasis. Other indications would include but are not limited to adult respiratory distress syndrome, reperfusion injury, ischemia, ulcerative colitis, vasculitides, atherosclerosis, inflammatory bowel disease, and tumor metastases.

Adhesion receptors are organized into three main families: the selectins, the immunoglobulin superfamily, and the integrins (*Nature* 346:426 (1990)). Members of all three classes are involved in mediating leukocyte adhesion during inflammation (for reviews of this area see: *Thrombosis and Hemostasis* 65(3):223 (1991), *Clinical and Experimental Allergy* 20:619 (1990), *Transplantation* 48:727 (1989), *Biochemical Pharm.* 40(8):1683 (1990)). Endothelial leukocyte adhesion molecule-1 (ELAM-1 or E-selectin) is a member of the selectin family of glycoproteins that promote cell-cell adhesion. ELAM-1 is reported to be maximally expressed on the surface of endothelial cells 4 hours after stimulation of the endothelial cells with cytokines, such as interleukin-1 (IL-1) or tumor necrosis factor α (TNF-α) or other inflammatory mediators, such as lipopolysaccharide (LPS) (*Pro. Nat. Acad. Sci.* 84:9238 (1987).

Intercellular adhesion molecule-1 (ICAM-1) is a member of the immunoglobulin superfamily. It is also upregulated with maximum expression occurring 12 to 24 hours after stimulus. It has been shown that 4 hours after the endothelial cells are stimulated with an inflammatory mediator, both ELAM-1 and ICAM-1 are present on the cell surface (*J. Clin. Invest.* 82:1746 (1988) and *J. Immun.* 137:1893 (1986), *Blood* 78:2721 (1991)).

The 3-alkyloxy-, aryloxy-, and arylalkyloxy-benzo[b]thiophene-2-carboxamides of the present invention have been shown in an in vitro assay to prevent the adhesion of neutrophils to human umbilical vein endothelial cells (HUVECS) stimulated with TNFα.

The 3-alkyloxy-, aryloxy-, and arylalkyloxy-benzo[b]thiophene-2-carboxamides of the present invention are new but are included in the generic scope of U.S. Pat. No. 4,800,211 as possible dual inhibitors of cyclooxygenase and 5-lipoxygenase. The specific compounds of the present invention do not significantly inhibit isolated 5-lipoxygenase.

SUMMARY OF THE INVENTION

Accordingly, the present invention is for the use of a compound of the formula (I) and pharmaceutically acceptable salts thereof to inhibit the adhesion of leukocytes to stimulated human endothelial cells, thereby providing for the treatment of inflammatory diseases:

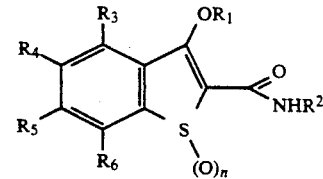

wherein
$R_1$ is lower alkyl, phenyl, or benzyl;
$R_2$ is hydrogen, lower alkyl, phenyl, benzyl, thiophene, $(CH_2)_mQ$, or phenyl, benzyl, or thiophene substituted with $(CH_2)_mQ$;
n is an integer from 0 to 2;
m is an integer from 0 to 6;
Q is $CO_2R_7$ where $R_7$ is hydrogen or lower alkyl; and
$R_3$, $R_4$, $R_5$, $R_6$ are independently hydrogen, hydroxy, nitro, amino, lower alkyl, and lower alkoxy.

Particularly, the present invention is the use of the following compounds in their free form or as pharmaceutically acceptable salts to treat inflammatory diseases by administering an effective amount in unit dosage form of:

5-methoxy-3-(1-methylethoxy)-benzo[b]thiophene-2-carboxamide;
3-(1-methylethoxy)-benzo[b]thiophene-2-carboxamide;
5-chloro-3-(1-methylethoxy)-benzo[b]thiophene-2-carboxamide;
5-methyl-3-(1-methylethoxy)-benzo[b]thiophene-2-carboxamide;
3-(1-methylethoxy)-5-nitro-benzo[b]thiophene 2-carboxamide;
7-methoxy-3-(1-methylethoxy)-benzo[b]thiophene-2-carboxamide;
3,5-dimethoxy-benzo[b]thiophene-2-carboxamide;
5-methoxy-3-(phenylmethoxy)-benzo[b]thiophene-2-carboxamide;
5-methoxy-3-(phenoxy)-benzo[b]thiophene-2-carboxamide;
5-hydroxy-3-(1-methylethoxy)-benzo[b]thiophene-2-carboxamide;
6-methoxy-3-(1-methylethoxy) benzo[b]thiophene-2-carboxamide;
4-[[[5-methoxy-3-(1-methylethoxy)benzo[b]thien-2-yl]carbonyl]amino]-benzoic acid;
3-[[[5-methoxy-3-(1-methylethoxy)benzo[b]thien-2-yl]carbonyl]amino]benzoic acid;
ethyl 2-[[[5-methoxy-3-(1-methylethoxy) benzo-b]thien-2-yl]carbonyl]amino]benzeneacetate
2-[[[5-methoxy-3-(1-methylethoxy)benzo[b]thien-2-yl]carbonyl]amino]benzoic acid;
4-[[[5-methoxy-3-(1-methylethoxy)benzo[b]thien-2-yl]carbonyl]aminomethyl]benzoic acid;
methyl 4-[[[5-methoxy-3-(1-methylethoxy)benzo-[b]thien-2-yl]carbonyl]amino]benzeneacetate;
4-[[[5-methoxy-3-(1-methylethoxy)benzo[b]thien-2-yl]carbonyl]amino]benzeneacetic acid;
methyl 3-[[[5-methoxy-3-(1-methylethoxy)benzo[b]thien-2-yl]carbonyl]amino]benzeneacetate;
3-[[[5-methoxy-3-(1-methylethoxy)benzo[b]thien-2-yl]carbonyl]amino]benzeneacetic acid;
methyl 5-[[[5-methoxy-3-(1-methylethoxy)benzo[b]thien-2-yl]carbonyl]amino]pentanoate;
5-[[[5-methoxy-3-(1-methylethoxy)benzo[b]thien-2-yl]carbonyl]amino]pentanoic acid;

3-[[[5-methoxy-3-(1-methylethoxy)benzo[b]thien-2-yl]carbonyl]amino2-thiophenecarboxylic acid;

5-methoxy N-methyl-(3-(1-methylethoxy)benzo[b]thiophene-2-carboxamide;

n-ethyl-(5-methoxy-3-(1-methylethoxy)benzo[b]thiophene-2-carboxamide;

5-methoxy-3-(1-methylethoxy)-N-phenyl-benzo[b]thiophene-2-carboxamide;

5-methoxy-3-(1-methylethoxy)-N-(phenylmethyl)benzo[b]thiophene-2-carboxamide;

5-methoxy-3-(1-methylethoxy)-benzo[b]thiophene-2-carboxamide-1-oxide;

5-methoxy 3-(1-methylethoxy)-benzo[b]thiophene2-carboxamide 1,1'-dioxide;

3-(1,1-dimethylethoxy)-5-methoxybenzo[b]thiophene-2-carboxamide;

6-chloro-3-(1-methylethoxy)benzo[b]thiophene-2-carboxamide;

5-amino-3-(1-methylethoxy)benzo[b]thiophene-2-carboxamide;

methyl 4-[[[5-methoxy-3-(1-methylethoxy)benzo[b]thien-2-yl]carbonyl]amino]butanoate;

4-[[[5-methoxy-3-(1-methylethoxy)benzo[b]thien-2-yl]carbonyl]amino]butanoic acid; or 5-methoxy-3-(1-methylethoxy)-N-(1-methylethyl)benzo[b]thiophene-2-carboxamide.

The present invention also includes the following novel compounds or their pharmaceutically acceptable acid addition salts thereof:

5-chloro-3-(1-methylethoxy)-benzo[b]thiophene-2-carboxamide;

5-methyl-3-(1-methylethoxy)-benzo[b]thiophene-2-carboxamide;

3-(1-methylethoxy)-5-nitro-benzo[b]thiophene 2-carboxamide;

7-methoxy-3-(1-methylethoxy)-benzo[b]thiophene-2carboxamide;

3,5-dimethoxy benzo[b]thiophene-2-carboxamide;

5-methoxy-3 (phenylmethoxy)-benzo[b]thiophene-2-carboxamide;

5-methoxy-3-(phenoxy)-benzo[b]thiophene-2-carboxamide;

5-hydroxy-3-(1-methylethoxy)-benzo[b]thiophene-2-carboxamide;

6-methoxy 3-(1-methylethoxy)-benzo[b]thiophene-2-carboxamide;

ethyl 2-[[[5-methoxy-3-(1-methylethoxy)benzo[b]thien-2-yl]carbonyl]amino]benzeneacetate;

4-[[[5-methoxy-3-(1-methylethoxy)benzo[b]thien-2-yl]carbonyl]aminomethyl]benzoic acid;

methyl 4-[[[5-methoxy-3-(1-methylethoxy)benzo[b]thien-2-yl]carbonyl]amino]benzeneacetate;

4-[[[5-methoxy-3-(1-methylethoxy)benzo[b]thien-2-yl]carbonyl]amino]benzeneacetic acid;

methyl 3-[[[5-methoxy-3-(1-methylethoxy)benzo[b]thien-2-yl]carbonyl]amino]benzeneacetate;

3-[[[5-methoxy-3-(1-methylethoxy)benzo[b]thien-2-yl]carbonyl]amino]benzeneacetic acid;

methyl 5-[[[5-methoxy-3-(1-methylethoxy)benzo[b]thien-2-yl]carbonyl]amino]pentanoate;

5-[[[5-methoxy-3-(1-methylethoxy)benzo[b]thien-2-yl]carbonyl]amino]pentanoic acid;

5-methoxy-N-methyl-(3-(1-methylethoxy)benzo[b]thiophene-2-carboxamide;

n-ethyl-(5-methoxy-3-(1-methylethoxy)benzo[b]thiophene-2-carboxamide;

5-methoxy-3-(1-methylethoxy)-N-phenyl-benzo[b]thiophene-2-carboxamide;

5-methoxy-3-(1-methylethoxy)-N-(phenylmethyl)benzo[b]thiophene-2-carboxamide;

5-methoxy-3-(1-methylethoxy)-benzo[b]thiophene-2-carboxamide-1-oxide;

5-methoxy-3-(1-methylethoxy)-benzo[b]thiophene-2-carboxamide 1,1'-dioxide;

3-(1,1-dimethylethoxy)-5-methoxybenzo[b]thiophene-2-carboxamide;

6-chloro-3-(1-methylethoxy)benzo[b]thiophene-2-carboxamide;

5-amino-3-(1-methylethoxy)benzo[b]thiophene-2-carboxamide;

methyl 4-[[[5-methoxy-3-(1-methylethoxy)benzo[b]thien-2-yl]carbonyl]amino]butanoate;

4-[[[5-methoxy-3-(1-methylethoxy)benzo[b]thien-2yl]carbonyl]amino]butanoic acid; or 5-methoxy-3-(1-methylethoxy)-N-(1-methylethyl)benzo[b]thiophene-2-carboxamide.

DETAILED DESCRIPTION

The terms used in defining the compounds of Formula I and the more particular compounds of the present invention are defined as follows:

Lower alkyl and lower alkoxy mean a straight or branched alkyl or alkoxy group having one to four carbon atoms and includes, for example, methyl, ethyl, propyl, i-propyl, or otherwise referred to as (methyl)ethyl, and t-butyl or otherwise referred to as 1,1-(dimethyl)ethyl, and correspondingly, for example, methoxy, ethoxy, i propoxy or otherwise referred to as 1-(methyl)ethoxy and the like.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge, S. M., et al, "Pharmaceutical Salts," *Journal of Pharmaceutical Science*, 66, pp. 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with inorganic or organic bases, such as metal bases or amines, such as alkali and alkaline earth metal bases, e.g., hydroxides or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science* 66:1-19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid form differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated form and are intended to be encompassed within the scope of the present invention.

In determining when a cell adhesion inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula I or pharmacologically acceptable salt thereof to achieve a therapeutic effect will, of course, vary both with the particular compound, the route of administration, the mammal under treatment, and the particular disorder of disease concerned. A suitable dose of a compound of Formula I or pharmacologically acceptable salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of arthritis or inflammation in general, due to any course, a suitable dose of a compound of Formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water in-oil emulsion. The active ingredient may also be in the form of a bolus, electuary, or paste.

The usefulness of the compounds of the present invention as inhibitors of leukocyte adherence to vascular endothelium, the 5-lipoxygenase enzyme, cyclooxygenase, and thus in treating inflammatory-related diseases or conditions may be demonstrated by their effectiveness in various standard test procedures. A description of each procedure and exemplary test results follows.

METHOD FOR DETERMINING THE INHIBITION OF HUMAN NEUTROPHIL ADHESION TO TNFα, IL-1α, AND LPS-STIMULATED HUMAN UMBILICAL VEIN ENDOTHELIAL CELLS BY 3-ALKYLOXY-, ARYLOXY, OR ARYLALKYLOXY-BENZO[b]THIOPHENE-2-CARBOXAMIDES

Isolation of Neutrophils

Neutrophils were isolated from anticoagulant-treated venous blood obtained from healthy human volunteers according to the method of Ferrante and Thong (*J. Immunol. Methods* 24:389 93 (1978)). The cell preparations consisted of greater than 98% neutrophils.

Endothelial Cell Culture

Second passage human umbilical vein endothelial cells (HUVEC) (Clonetics, San Diego, Calif.) were seeded into Falcon 24-well cell culture plates (Becton Dickinson, Lincoln Park, N.J.) at approximately $2 \times 10^4$ cells per well. The cells were grown to confluent monolayers in endothelial basal medium (EBM, Clonetics) supplemented with 5% fetal calf serum (Hyclone Laboratories, Logan, Utah), 10 ng/mL EGF, 1 μg/mL hydrocortisone, 0.4% bovine brain extract (Clonetics) in 5% $CO_2$ at 37° C.

Neutrophil Adhesion

Neutrophils ($30 \times 10^6$) were labeled for 60 minutes at 37° C. with 100 μCi $Na^{51}CrO_4$ (ICN Biomedicals, Costa Mesa, Calif.) in 2.0 mL $Ca^{2+}$- and $Mg^{2+}$-free Hanks' balanced salt solution (HBSS, GIBCO Laboratories, Grand Island, N.Y.). The cells were washed two times in HBSS and suspended in unsupplemented EBM.

Stimulation of HUVEC with tumor necrosis factor-α (TNFα) (Genzyme, Cambridge, Mass.), interleukin (IL-1α) (Genzyme) or *E. coli* 0111:B4 lipopolysaccharide (LPS) (Sigma) in the presence or absence of drug was initiated 4 hours prior to the addition of neutrophils. The suspension medium was unsupplemented EBM or supplemented EBM for studies with cytokines or LPS, respectively. Such treatment has been shown to promote maximal expression of the endothelial cell-leukocyte adhesion molecule ELAM-1 as well as expression of ICAM-1 (*J. Immunol.* 137:1893 (1986); *Proc. Natl. Acad. Sci. USA* 9238 (1987)). Immediately prior to addition of $^{51}Cr$-labeled neutrophils to the HUVEC monolayers, the cultures were washed with 1 mL unsupplemented media to remove stimulus and/or drug. Neutrophils ($5 \times 10^5$) were then added to the HUVEC in 0.5 mL unsupplemented media and incubated at 37° C. for 30 minutes. Nonadherent neutrophils were removed by aspiration. Following an additional wash, adherent neutrophils were lysed with 0.5 mL 1N $NH_4OH$ overnight at 37° C. Lysates were collected and the radioactivity in each well was determined by gamma ray spectroscopy. The results obtained with certain compounds of the present invention are shown in Tables 1-3.

TABLE 1

Inhibition of Adhesion by 3-Alkoxy-benzo[b]thiophene-2-primary carboxamides

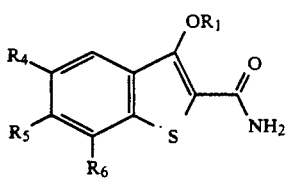

| Example Number | $R_1$ | $R_4$ | $R_5$ | $R_6$ | Adhesion (% Inhibition at 100 μM or $IC_{50}$, μM) |
|---|---|---|---|---|---|
| 1 | i-Pr | OMe | H | H | 3.8 |
| 2 | i-Pr | H | H | H | (60%) |
| 3 | i-Pr | Cl | H | H | (72%) |
| 4 | i-Pr | Me | H | H | (61%) |
| 5 | i-Pr | $NO_2$ | H | H | (40%) |
| 6 | i-Pr | H | H | OMe | (35%) |
| 7 | Me | OMe | H | H | (60%) |
| 8 | $CH_2Ph$ | OMe | H | H | (57%) |
| 9 | Ph | OMe | H | H | (59%) |
| 10 | i-Pr | OH | H | H | 1.2 |

TABLE 1-continued

Inhibition of Adhesion by 3-Alkoxy-benzo[b]thiophene-2-primary carboxamides

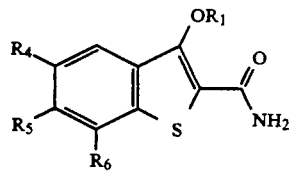

| Example Number | $R_1$ | $R_4$ | $R_5$ | $R_6$ | Adhesion (% Inhibition at 100 μM or $IC_{50}$, μM) |
|---|---|---|---|---|---|
| 11 | i-Pr | H | OMe | H | (24%) |
| 30 | t-Bu | OMe | H | H | (100%) |
| 31 | i-Pr | H | Cl | H | (26%) |
| 32 | i-Pr | $NH_2$ | H | H | (49%) |

TABLE 2

Inhibition of Adhesion by 3-Alkoxy-benzo[b]thiophene-2-substituted carboxamides

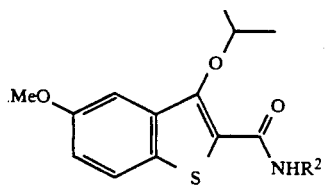

| Example Number | $R^2$ | Adhesion (% Inhibition at 100 μM or $IC_{50}$, μM) |
|---|---|---|
| 1 | H | 3.8 |
| 12 | Ph-p-COOH | 50 |
| 13 | Ph-m-COOH | (28%) |
| 14 | Ph-o-COOEt | (32%) |
| 15 | Ph-o-COOH | (35%) |
| 16 | $CH_2$Ph-p-COOH | (47%) |
| 17 | Ph-p-$CH_2$COOMe | (27%) |
| 18 | Ph-p-$CH_2$COOH | (32%) |
| 19 | Ph-m-$CH_2$COOMe | (45%) |
| 20 | Ph-m-$CH_2$COOH | (70%) |
| 21 | $(CH_2)_4$COOMe | (8%) |
| 22 | $(CH_2)_4$COOH | (9%) |
| 23 | thiophene-2-COOH | (20%) |
| 24 | Me | (78%) |
| 25 | Et | (64%) |
| 26 | Ph | (12%) |
| 27 | $CH_2Ph$ | (35%) |
| 33 | $(CH_2)_3$COOMe | (100%) |
| 34 | $(CH_2)_3$COOH | (35%) |
| 35 | i-Pr | (100%) |

TABLE 3

Inhibition of Adhesion by 2-Carboxamide-
3-isopropoxy-5-methoxy-benzo[b]thiophene-
mono-oxy and di-oxy Analogs

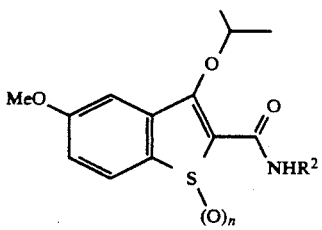

| Example Number | n | Adhesion (% Inhibition at 100 μM or IC$_{50}$, μM) |
| --- | --- | --- |
| 1 | 0 | 3.8 |
| 28 | 1 | (83%) |
| 29 | 2 | (4%) |

One of the above compounds, 5-methoxy-3-(1-methylethoxy)-benzo[b]thiophene-2-carboxamide, also gave potent inhibition of the human one way mixed lymphocyte reaction (MLR). The compound has an IC$_{50}$ of 0.3 μM (n=2). The details of this assay are as follows:

Method for Determining the Inhibition of the Human One-Way Mixed Lymphocyte Reaction by 5-Methoxy-3-(1-methylethoxy)benzo[b]thiophene-2-carboxanide

Lymphocyte Isolation

All methods were adapted from published procedures (references below). Heparinized peripheral blood was collected from normal human donors. Lymphocytes were isolated by density gradient centrifugation on Ficoll-Hypaque gradients (10 mL blood to 4 mL Ficoll-Hypaque, specific gravity =1.09 mg/mL, Pharmacia) for 20 minutes at 1200×g at room temperature. Lymphocytes (top layer) were removed and washed three times with Hanks balanced salt solution (HBSS) without magnesium and calcium (MA Bioproducts), centrifuging for 10 minutes at 300 g. Cell viability was determined using trypan blue exclusion. Cells were kept on ice until added to culture plates.

Culture Medium

The final culture medium consisted of RPMI 1640 (Microbiological Associates) supplemented with L-glutamine (2 mM), penicillin (100 IU/mL), streptomycin (100 μg/mL), HEPES buffer (10 mM), and 10% heat inactivated (56° C., 30 minutes) fetal calf serum (FCS) (Armour).

One-Way Mixed Lymphocyte Reaction (MLR) Cultures

Lymphocytes which were used as stimulators were treated with mitomycin C (50 μg/mL/10$^7$ cells) for 20 minutes at 37° C. Cells were washed twice with HBSS not containing magnesium and calcium. Responder cells (50 μL at 8×10$^6$ cells/mL in 40% FCS) were added to 96-well microtiter plate wells with an equal volume and number of allogeneic, mitomycin C-treated stimulator cells (not in FCS). Test materials and media were added in 50 μL aliquots each, such that the final culture conditions were 2×10$^6$ responding cells/mL (4×10$^5$ responding cells/well) in medium containing 10% FCS. Unstimulated responder cells were run as background controls in medium alone and with compound dilutions. Cultures were pulsed with 0.5 μCi $^3$H-thynidine for the final 6 hours of a 6-day incubation period. Cultures were harvested and counted as above using an automatic cell harvester and standard liquid scintillation counting.

The inhibition of cyclooxygenase and 5-lipoxygenase by certain of the compounds of the present invention are shown in Table 4. The testing methods used are described as follows:

TABLE 4

Inhibition of 5-Lipoxygenase and Cyclooxygenase
by 3-Alkoxy-benzo-[b]thiophene-2-carboxamides

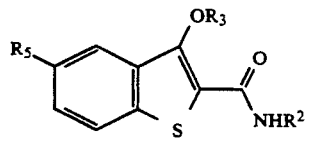

| Number | R | R-3 | R-5 | ARBL/ARBC IC$_{50}$ (μM) or % Inhibition at 10 μM | 5-LO (% Inhibition at 30 μM) |
| --- | --- | --- | --- | --- | --- |
| 1 | H | iPr | OMe | 36 | 13% |
| 12 | Ph-p-COOH | iPr | OMe | 36/89 | 16% |
| 2 | H | iPr | H | N/N | NA |
| 9 | H | Ph | OMe | N/N | NA |

N = Less than 40% inhibition at 10 μM
NA = Less than 4% inhibition at 30 μM

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of LTB$_4$ and PGF$_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate-buffered saline, pH 7.4 (PBS; NaCl, 7.1 g; Na$_2$HPO$_4$, 1.15 g; KH$_2$PO$_4$, 0.2 g; and KCl, 0.2 g/L). Cells are finally suspended in PBS containing 1.0 mM calcium at a density of 2×10$^6$ cells/mL. Cells are incubated and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at −20° C. Aliquots (100 μL) are analyzed for LTB$_4$ and PGF$_{2\alpha}$ using radioimmunoassay kits as provided by the supplier.

PROTOCOL FOR 5-LIPOXYGENASE INHIBITION ASSAY

Compounds are evaluated for inhibition of 5-lipoxygenase activity contained in the 20,000 xg supernatant from cultured rat basophilic leukemia (RBL) cells. Incubations contained 5% (v/v) RBL 20,000 xg supernatant in assay buffer (10 mM BES, 10 mM PIPES, 1 mM EDTA, 0.75 mM $CaCl_2$, 1 mM ATP, 100 mM NaCl, pH 6.8). DMSO vehicle (2% v/v) with and without inhibitors is preincubated with the enzyme for 20 minutes at 37° C. before initiating the 5-lipoxygenase catalyzed reaction by adding 3.3 nmol [$^{14}$C]arachidonic acid (55.8 mCi/mmole, New England Nuclear, Boston, Mass.) dissolved in 5 μL 0.028% (v/v) aqueous $NH_4OH$. After 20 minutes of additional incubation at 37° C., reactions are terminated by the addition of three volumes of methanol containing 100 μg triphenylphosphine. Samples are then analyzed by HPLC with radiometric detection for 5-lipoxygenase reaction products.

All treatments are evaluated in duplicate and percent inhibition is computed by comparing the products formed in treatment incubations to the mean product formation in the vehicle control group. The 50% inhibitory concentration ($IC_{50}$) values are computed by regression analysis of the linear portion of percentage inhibition of 5-HETE formation vs $log_{10}$ inhibitor concentration curves.

The compounds of the present invention where $R_2$ is hydrogen are preferably prepared from the corresponding benzo[b]thiophene-2 carboxylic acids. The starting carboxylic acids are prepared as described in U.S. Pat. No. 4,703,503, which is incorporated herein by reference. As depicted in Scheme 1 below, the benzo[b]thiophene-2-carboxylic acid is first treated with a coupling agent, preferably 1,1'-carbonyldiimidazole (CDI), in a solvent such as tetrahydrofuran or acetonitrile to form the corresponding imidazolide or other leaving group. Alternatively, the benzo[b]thiophene-2-carboxylic acid is converted to the acid halide via a reagent such as thionyl chloride, or preferably oxalyl chloride with a catalytic amount of dimethylformamide in a solvent such as methylene chloride or tetrahydrofuran. Subsequent reaction with aqueous ammonium hydroxide or ammonia gas gives the desired primary benzo[b]thiophene 2 carboxamides.

The primary amides can also be prepared by treatment of the corresponding benzo[b]thiophene-2-carboxylic acid ester with lithium amide in liquid ammonia in the presence of a co solvent such as tetrahydrofuran.

Reaction with an oxidizing agent, preferably hydrogen peroxide in acetic acid, converts the benzo[b]thiophene 2-carboxamides to the benzo[b]thiophene 2-carboxamide 1-oxides or benzo[b]-thiophene-2-carboxamide-1,1'-dioxides depending on the conditions used. With increased temperature or an excess of oxidizing agent the benzo[b]thiophene-2-carboxamide-1-oxides are further oxidized to the benzo[b]thiophene 2 carboxamide 1,1'-dioxides.

Conditions within the description of Scheme 1 and variations in the description are known or can readily be determined from analogous reactions known to one skilled in the art.

SCHEME 1

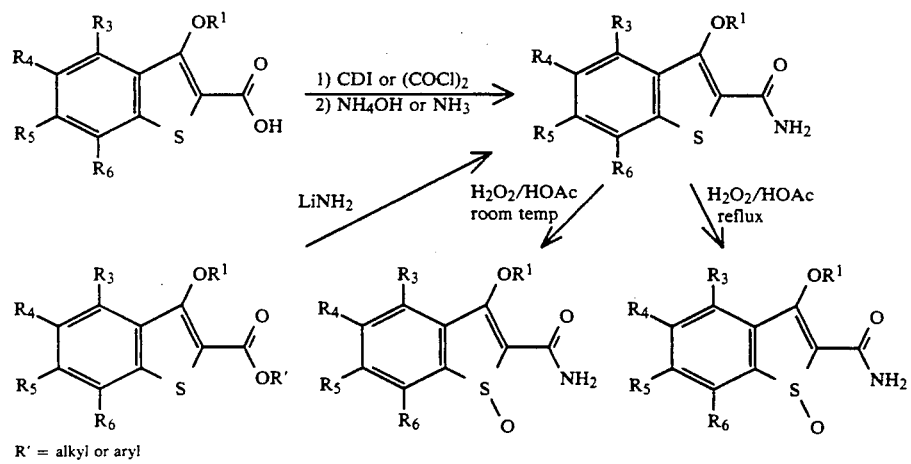

As depicted in Scheme 2, a similar procedure is used to prepare the secondary benzo[b]thiophene-2-carboxamides. Instead of aqueous ammonium hydroxide, the intermediate imidazolide or acid chloride is reacted with a primary amine in the presence or absence of a base such as triethylamine or 1,8-diazabicyclo[5.4.0]-undec-7-ene (DBU). When the amine is in the form of its HCl salt, additional base is required to obtain the free amine.

Once again, by modification of the oxidizing conditions, the 1-oxide or the 1,1'-dioxide analogs can be obtained. Conditions within the description of Scheme 2 and variations in the description are known or can readily by determined from analogous reactions known to one skilled in the art.

SCHEME 2

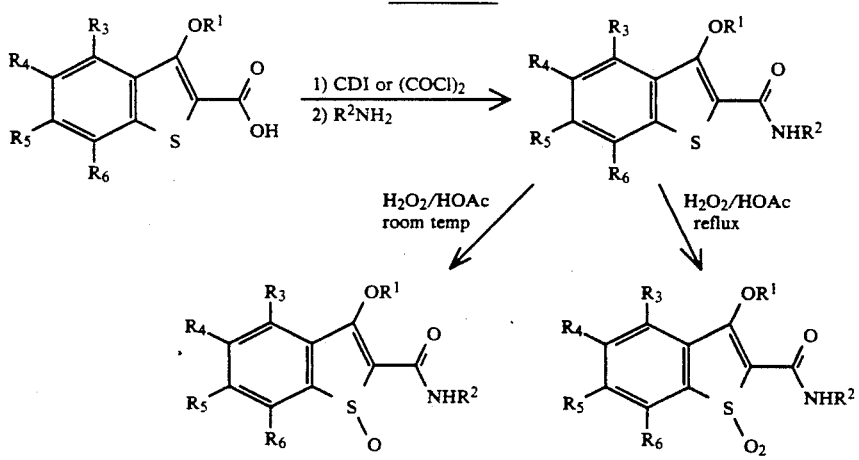

Scheme 3 shows the preparation of secondary benzo[b]thiophene-2-carboxamides containing a carboxylic acid functionality. These compounds are prepared via an intermediate ester. As in Scheme 2, the benzo[b]thiophene-2-carboxylic acid is activated and then treated with an amine that contains the desired ester residue. The amine can be in the form of its HCl salt. The intermediate is isolated and the ester functionality is hydrolyzed, preferably with sodium hydroxide in aqueous ethanol, to give the desired carboxylic acid.

SCHEME 3

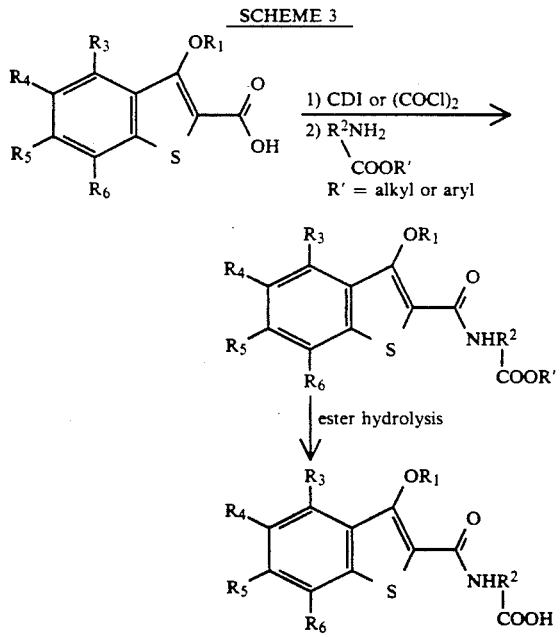

Those compounds where one or more of $R_3$–$R_6$ is hydroxy are prepared via an intermediate that has a suitable hydroxy protecting group. As an example, Scheme 4 shows the preparation of 5-hydroxy-benzo[b]thiophene-2-carboxamides. The amides are prepared from the corresponding acid containing a hydroxy group protected as its benzyl ether. The benzyl group is then removed, preferably by hydrogenation. Other protecting groups, such as silyl groups, can also be used and later removed using standard methodology.

SCHEME 4

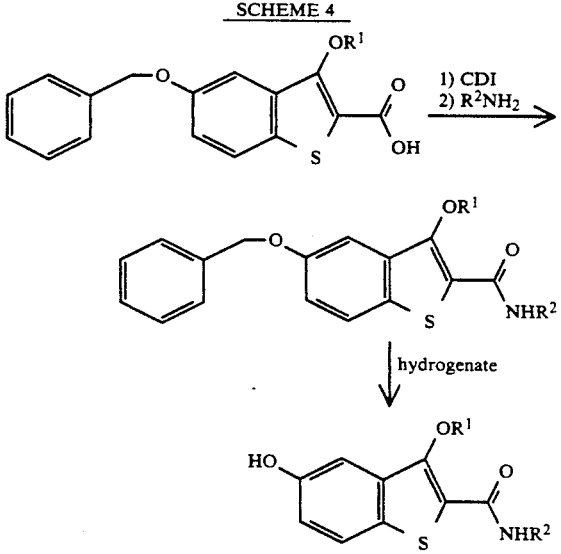

The following examples are illustrative of the preparation of the compounds of the present invention.

EXAMPLES

EXAMPLE 1

The preparation of 5-methoxy-3-(1-methylethoxy)-benzo[b]thiophene-2-carboxamide is found in U.S. Pat. No. 4,703,053.

EXAMPLE 2

The preparation of 3-(1-methylethoxy)-benzo[b]thiophene-2-carboxamide is found in U.S. Pat. No. 4,703,053.

General procedure for the preparation of primary benzo[b]thiophene-2-carboxamides from the corresponding benzo[b]thiophene-2-carboxylic acid.

This procedure was used to prepare Examples 3 to 9 and also 30 to 31. For the preparation of the acids see U.S. Pat. No. 4,703,053.

To 1 mM of a suitably substituted benzo[b]thiophene-2-carboxylic acid in 10 mL of dry tetrahydrofuran is added 1.3 mM of N,N-carbonyldiimidazole. The solution is heated at reflux for 1 hour, then allowed to cool to room temperature. An excess of aqueous ammonium hydroxide (2 mL) is added and the solution is stirred at room temperature for 30 minutes. The mixture is partitioned between ethyl acetate and brine. The organic layer is dried over magnesium sulfate, filtered, and concentrated in vacuo. The crude product is purified by flash chromatography, eluting with 1:1 hexane:ethyl acetate to provide the desired benzo[b]thiophene-2-carboxamides as analytically pure materials.

EXAMPLE 3

5-Chloro-3-(1-methylethoxy)-benzo[b]thiophene-2-carboxamide (92%); mp 165°–167° C.

EXAMPLE 4

5-Methyl-3-(1-methylethoxy)-benzo[b]thiophene-2-carboxamide (94%); mp 153°–154° C.

EXAMPLE 5

3-(1-methylethoxy)-5-nitro-benzo[b]thiophene-2-carboxamide (85%); mp 205°–207° C.

EXAMPLE 6

7-Methoxy-3-(1-methylethoxy)-benzo[b]thiophene-2-carboxamide (91%); mp 157°–159° C.

EXAMPLE 7

3,5-Dimethoxy-benzo[b]thiophene-2-carboxamide (70%); mp 184°–185° C.

EXAMPLE 8

5-Methoxy-3-(phenylmethoxy)-benzo[b]thiophene-2-carboxamide (72%); mp 149°–151° C.

EXAMPLE 9

Note: Instead of 1,1'-carbonyldiimidazole, the corresponding acid was treated with oxalyl chloride, then with aqueous ammonium hydroxide.

5-Methoxy-3-(phenoxy)-benzo[b]thiophene 2-carboxamide (84%); mp 197.5°–198.5° C.

EXAMPLE 10

5-Hydroxy-3-(1-methylethoxy)-benzo[b]thiophene-2-carboxamide

A mixture of 3-(1-methylethoxy)-5-phenylmethoxy)-benzo[b]thiophene-2-carboxamide (120 mg, 0.35 mmoles) [prepared via the general method given above] and 20% Pd on carbon (50 mg) in 40 mL of acetic acid is hydrogenated for 72 hours. The catalyst is removed by filtration and the filtrate concentrated in vacuo. The crude product is chromatographed, eluting with a gradient of 1:1 to 1:2 hexane:ethyl acetate, providing 49.4 mg of 5-hydroxy-3-(1-methylethoxy)-benzo[b]thiophene-2-carboxamide (56%); mp 237°–240° C. (dec).

EXAMPLE 11

6-Methoxy-3-(1-methylethoxy)-benzob]thiophene-2-carboxamide

Excess lithium (74 mg, 10 mM) is added 120 portionwise to a −78° C. solution of a catalytic amount of ferric nitrate in 10 mL of liquid ammonia. The dry ice-/acetone bath is removed to allow the reaction to warm to reflux. When the gray color of lithium amide remains for 10 minutes, 2 mL of freshly distilled tetrahydrofuran is added slowly followed by a solution of methyl 6-methoxy-3-(1 methylethoxy)-benzo[b]thiophene-2-carboxylic acid (200 mg, 0.71 mM) in 2 mL of tetrahydrofuran. The ammonia is allowed to evaporate. The reaction solution is diluted with ethyl acetate, washed with aqueous hydrochloric acid, followed by water, then brine. The organic phase is dried over magnesium sulfate, filtered, and concentrated in vacuo. The crystalline residue is suspended in 1:9 ethyl acetate:hexane, filtered, and dried at 50° C. in vacuo affording 125 mg (66%) of colorless crystals, mp 164°–166° C.

EXAMPLE 12

4-[[[5-Methoxy-3-(1-methylethoxy)benzo[b]thien-2-yl]-carbonyl]amino]-benzoic acid To 5-methoxy-3-(1-methylethoxy)benzo[b]-thiophene-2-carboxylic acid (353 mg, 1.32 mmoles) in 5 mL of dry tetrahydrofuran is added oxalyl chloride (140 μL, 1.60 mmoles) followed by one drop of dimethylformamide. The solution is stirred at room temperature for 1 hour, then concentrated in vacuo. The resulting solid is added portionwise to a 0° C. solution of methyl 4-amino-benzoate (250 mg, 1.65 mmoles) and triethylamine (220 μL, 1.58 mmoles) in 10 mL of tetrahydrofuran. The mixture is stirred at room temperature for 1 hour, then partitioned between ethyl acetate and brine. The organic layer is dried over magnesium sulfate, filtered, and concentrated in vacuo. The crude product is purified by flash chromatography, eluting with 3:1 hexane:ethyl acetate to provide 284 mg of product, mp 138°–142° C.

A mixture of 4.0 g of methyl 4-[[[5-methoxy-3-(1-methylethoxy)-benzo[b]thien-2-yl]carbonyl]amino]benzoate and 2 g of 50% NaOH in 100 mL of 10% aqueous methanol is heated on a steam bath for 15 minutes, then poured onto ice and acidified with 10% HCl. The resulting gum is extracted into 500 mL of diethyl ether. The organic phase is dried over magnesium sulfate, filtered, and concentrated in vacuo. The crude solid is triturated with t-butyl methyl ether to provide 2.5 g of product; mp 236°–239° C. (dec).

EXAMPLE 13

3-[[[5-Methoxy-3-(1 methylethoxy)benzo[b]thien-2-yl]carbonyl]amino]benzoic acid

Following a procedure analogous to Example 12, 5-methoxy-3-(1-methylethoxy)-benzo[b]thiophene-2-carboxylic acid (7.0 g, 26 mmoles) and ethyl 3-amino benzoate (4.3 g, 26 mmoles) provides 8.5 g (78%) of the intermediate ester. Saponification of the crude ester followed by recrystallization from aqueous ethanol gives 4.2 g (53%) of product; mp 197°–200° C. (dec).

EXAMPLE 14

Ethyl 2-[[[5-methoxy-3-(1-methylethoxy)benzo[b]thien-2yl]-carbonyl]amino]benzeneacetate Following a procedure analogous to Example 12, 5-methoxy-3-(1-methylethoxy)benzo[b]thiophene-2-carboxylic acid (1.04 g, 3.9 mmoles) and ethyl 2-amino benzoate (.67 g, 4.1 mmoles) provides 0.81 g (51%) of product; mp 105°–106° C.

EXAMPLE 15

2-[[[5-Methoxy-3-(1-methylethoxy)benzo[b]thien-2-yl]carbonyl]amino]benzoic acid

Saponification of 0.25 g of ethyl 2-[[[5-methoxy-3-(1-methylethoxy)benzo[b]thien-2-yl]carbonyl]amino]benzeneacetate gives 0.17 g (72%) of product; mp 239°-242° C. (dec).

EXAMPLE 16

4-[[[5-Methoxy-3-(1 methylethoxy)benzo[b]thien-2-yl]carbonyl]aminomethyl]benzoic acid A solution of 5-methoxy-3-(1-methylethoxy)benzo[b]thiophene-2-carboxylic acid (500 mg, 2.00 mmoles) and 1,1'-carbonyldiimidazole (421 mg, 2.60 mmoles) in 20 mL of tetrahydrofuran is heated at reflux for 1 hour. After cooling to 0° C., the HCl salt of methyl 4-(aminomethyl)-benzoate (524 mg, 2.6 mmoles) is added followed by triethylamine (362 µL, 2.6 mmoles). The mixture is stirred at room temperature for 4 hours. The mixture is partitioned between ethyl acetate and 1N HCl. The organic layer is washed with water, then brine. The organic layer is next dried over magnesium sulfate, filtered, and concentrated in vacuo. The crude product is purified by flash chromatography, eluting with a gradient of 1:9 to 15:85 ethyl acetate:methylene chloride to provide 49 mg of the desired intermediate ester. The ester and 15 mg of LiOH-H₂O in 2 mL of 50% aqueous methanol are heated at reflux for 1 hour. The organic layer is washed with water, then brine, dried over magnesium sulfate, filtered, and concentrated in vacuo. Recrystallization from ethyl acetate:hexane gives 32.1 mg of product (65% from the ester); mp 142°-143° C. (dec).

EXAMPLE 17

Methyl 4-[[[5-Methoxy-3-(1-methylethoxy)benzo[b]thien-2-yl]carbonyl]amino]benzeneacetate To 5-methoxy-3-(1-methylethoxy)benzo[b]thiophene-2-carboxylic acid (500 mg, 2.0 mmoles) in 20 mL of dry tetrahydrofuran is added oxalyl chloride (262 µL, 3.0 mmoles) followed by one drop of dimethylformamide. The HCl salt of methyl 4-aminophenylacetate (605 mg, 3.0 mmoles) is added, followed by triethylamine (1.4 mL, 10 mmoles). The mixture is stirred at room temperature overnight. The mixture is partitioned between ethyl acetate and 1N HCl. The organic layer is washed with water, then brine. The organic layer is next dried over magnesium sulfate, filtered, and concentrated in vacuo. The crude product is purified by flash chromatography, eluting with a gradient of 1:1 ethyl acetate:hexane to only ethyl acetate to provide 692 mg (84%) of product; mp 111°-113° C.

EXAMPLE 18

4-[[[5-Methoxy-3-(1-methylethoxy)benzo[b]thien-2-yl]carbonyl]amino]benzeneacetic acid Methyl 4-[[[5-methoxy-3-(1-methylethoxy)benzo[b]thien-2-ylcarbonyl]amino]phenylacetate (300 mg, 0.73 mmoles) and 91 mg of LiOH-H₂O in a mixture of 5 mL of methanol and 2 mL of water are heated at reflux for 2 hours. The reaction mixture is partitioned between ethyl acetate and aqueous HCl. The organic layer is washed with water, then brine, dried over magnesium sulfate, filtered, and concentrated in vacuo. Recrystallization from ethyl acetate:hexane gives 247 mg (85%) of product; mp 195.5°-196.5° C.

EXAMPLE 19

Methyl 3-[[[5-Methoxy-3-(1-methylethoxy)benzo[b]thien-2-yl]carbonyl]amino]benzeneacetate Following a procedure analogous to that of Example 17; 5-methoxy-3-(1-methylethoxy)benzo[b]thiophene-2-carboxylic acid (500 mg, 2.0 mmoles) and the HCl salt of methyl 3-aminophenylacetate (605 mg, 3.00 mmoles) provide 506 mg (61%) of product; mp 103°-106° C.

EXAMPLE 20

3-[[[5-Methoxy-3-(1-methylethoxy)benzo[b]thien-2-yl]carbonyl]amino]benzeneacetic acid Following a procedure analogous to that of Example 18; methyl 3-[[[5-methoxy 3-(1-methylethoxy)benzo[b]thien-2-yl]carbonyl]amino]phenylacetate (250 mg, 0.60 mmoles) and 76 mg of LiOH-H₂O provide 172 mg (72%) of product; mp 155°-156° C.

EXAMPLE 21

Methyl 5-[[[5-methoxy-3-(1-methylethoxy)benzo[b]thien-2-yl]carbonyl]amino]pentanoate A solution of 5-methoxy-3-(1-methylethoxy)benzo[b]thiophene-2-carboxylic acid (500 mg, 2.00 mmoles) and 1,1'-carbonyldiimidazole (421 mg, 2.60 mmoles) in 20 mL of tetrahydrofuran is heated at reflux for 1 hour. After cooling to 0° C., the HCl salt of methyl 5-aminovalerate (787 mg, 4.7 mmoles) is added followed by triethylamine (836 µL, 6.0 mmoles). The mixture is heated at reflux overnight. The mixture is partitioned between ethyl acetate and 1N HCl. The organic layer is washed with 1N HCl, saturated NaHCO₃, then brine. The organic layer is next dried over magnesium sulfate, filtered, and concentrated in vacuo. The crude product is purified by flash chromatography, eluting with 1:9 ethyl acetate:hexane to provide 530 mg (70%) of product; mp 82°-84° C.

EXAMPLE 22

5-[[5-Methoxy-3-(1-methylethoxy)benzo[b]thien-2-yl]carbonyl]amino]pentanoic acid Methyl 5-[[5-methoxy-3-(1-methylethoxy)benzo[b]thien-2-yl]carbonyl]amino-valerate (250 mg, 0.66 mmoles) and 83 mg of LiOH H₂O in a mixture of 5 mL of methanol and 2 mL of water are stirred at room temperature for 7 hours. The reaction mixture is partitioned between ethyl acetate and aqueous HCl. The organic layer is washed with water, then brine, dried over magnesium sulfate, filtered, and concentrated in vacuo. Recrystallization from ethyl acetate:hexane gives 205 mg of product (85%); mp 135°-137° C.

EXAMPLE 23

3-[[[5-Methoxy-3-(1-methylethoxy)benzo[b]thien-2-yl]carbonyl]amino-2-thiophenecarboxylic acid To 5-methoxy-3-(1-methylethoxy)benzo[b]thiophene-2-carboxylic acid (7.0 g, 26 mmoles) in 100 mL of dry tetrahydrofuran is added oxalyl chloride (2.8 mL, 32 mmoles) followed by 4 drops of dimethylformamide. The solution is stirred at room temperature for 45 minutes, then concentrated in vacuo. The resulting solid is dissolved in dry tetrahydrofuran and added dropwise to a solution of methyl 3-amino-2-thiophenecarboxylate (4.5 g, 29 mmoles) and triethylamine (11 mL, 79 mmoles) in 75 mL of tetrahydrofuran. The mixture is stirred at room temperature for 2 hours, then quenched with 10% HCl. The mixture is extracted with ethyl acetate, and the combined organic layers washed with 5% sodium bicarbonate and brine. The organic layer is dried over magnesium sulfate, filtered, and concentrated in vacuo. The crude product is recrystallized from t-butyl methyl ether to provide 4.5 g of a white solid; mp 131°–137° C.

4.4 g (11 mmoles) of this ester is combined with 50% aqueous sodium hydroxide (4.0 g, 50 mmoles) in 10% aqueous methanol (200 mL) and 40 mL of tetrahydrofuran. The mixture is heated on the steam bath for 2 hours, cooled, and added to 60 g of ice. After acidification with 10% HCl, the precipitated solid is filtered and washed with water. Recrystallization from 95% ethanol gives 3.0 g (71%) of product; mp 223°–227° C. (dec).

General procedure for the preparation of secondary benzo[b]thiophene-2-carboxamides from the corresponding acid:

A solution of 1 mM of a suitably substituted benzothiophene-2-carboxylic acid and 1.3 mM of 1,1'-carbonyldiimidazole in dry tetrahydrofuran is refluxed for 1 to 2 hours. The reaction solution is cooled to 0° C. and an excess amount of a primary amine is added. The reaction is diluted with ethyl acetate and washed with aqueous hydrochloric acid, followed by water, then brine. The organic phase is dried over magnesium sulfate, filtered, and concentrated in vacuo. Analytical products are obtained via column chromatography and/or recrystallization.

EXAMPLE 24

5-Methoxy-N-methyl-(3-(1-methylethoxy)benzo[b]thiophene-2-carboxamide (55%); mp 104°–105° C.

EXAMPLE 25

N-Ethyl-(5-methoxy 3-(1-methylethoxy)benzo[b]thiophene-2-carboxamide (62%); mp 60°–62° C.

EXAMPLE 26

5-Methoxy-3-(1-methylethoxy)-N-phenyl-benzo[b]thiophene-2-carboxamide (27%); mp 116°–118° C.

EXAMPLE 27

5-Methoxy-3-(1-methylethoxy) N-(phenylmethyl)benzo[b]thiophene-2-carboxamide (81%); mp 85°–86° C.

EXAMPLE 28

5-Methoxy-3-(1-methylethoxy)-benzo[b]thiophene-2-carboxamide-1-oxide

A solution of 5-methoxy 3-(1-methylethoxy)benzothiophene-2-carboxamide (250 mg, 0.94 mM) and 30% hydrogen peroxide (4 mL, 40 mM) in acetic acid (9.5 mL) is stirred at room temperature for 8 hours. The reaction solution is diluted with water and the pH is adjusted to 7 with aqueous sodium hydroxide and saturated sodium bicarbonate. The organic materials are extracted with ethyl acetate. The organic phase is washed with a saturated solution of sodium bicarbonate, followed by water, then brine, and dried over magnesium sulfate, filtered, and concentrated in vacuo. The residue is crystallized twice from ethyl acetate:hexane to give 60 mg (23%) of the 1-oxide; mp 163°–164° C.

EXAMPLE 29

5-Methoxy-3-(1-methylethoxy) benzo[b]thiophene-2-carboxamide 1,1'-dioxide

A solution of 5-methoxy-3-(1-methylethoxy)benzothiophene-2-carboxamide (250 mg, 0.94 mM) and 30% hydrogen peroxide (4 mL, 40 mM) in acetic acid (9.5 mL) is heated at reflux for 6 hours. The reaction solution is diluted with ethyl acetate and washed 5 times with brine, dried over magnesium sulfate, filtered, and concentrated in vacuo. The residue is crystallized from ethyl acetate:hexane to give 67 mg (24%) of the dioxide; mp 151°–153° C.

EXAMPLE 30

3-(1,1-Dimethylethoxy)-5-methoxybenzo[b]thiophene-2-carboxamide

Prepared by a procedure analogous to Example 2 (74%); mp 180°–181° C.

EXAMPLE 31

6Chloro-3-(1-methylethoxy)benzo[b]thiophene-2-carboxamide

Prepared by a procedure analogous to Example 2 (90%); mp 176°–178° C.

EXAMPLE 32

5-Amino-3-(1-methylethoxy)benzo[b]thiophene-2-carboxamide

A mixture of 3-(1-methylethoxy)-5-nitrobenzo[b]thiophene-2-carboxamide (104 mg, 0.37 mmoles) and 5% Pd on carbon (10 mg) in 20 mL of acetic acid is hydrogenated for 1.5 hours. The catalyst is removed by filtration and the filtrate concentrated in vacuo. The crude product is chromatographed, eluting with 1:2 hexane:ethyl acetate, providing 62 mg of 5 amino 3 (1 methylethoxy)-benzo[b]-thiophene-2-carboxamide (67%); mp 150°–151° C.

EXAMPLE 33

Methyl 4-[[[5-methoxy-3-(1-methylethoxy)benzo[b]thien-2-yl]carbonyl]amino]butanoate Prepared by a procedure analogous to Example 21 (93%); mp 35°–36.5° C.

EXAMPLE 34

4-[[[5-Methoxy-3-(1-methylethoxy)benzo[b]thien-2-yl]carbonyl]amino]butanoic acid Prepared by a procedure analogous to Example 22 (77%); mp 101°–102° C. (dec).

EXAMPLE 35

5-Methoxy-3-(1-methylethoxy)-N-(1-methylethyl)benzo[b]thiophene-2-carboxamide

Prepared by a procedure analogous to Example 24 (76%); mp 64.5°–65.5° C.

We claim:

1. A method of treating diseases mediated by inhibiting the adhesion of leukocytes to endothelial cells comprising administering to a host in need thereof an effective amount in unit dosage form of a compound of the formula

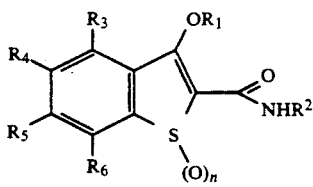

wherein

R₁ is lower alkyl, phenyl, or benzyl;

R₂ is hydrogen, lower alkyl, phenyl, benzyl, thiophene, $(CH_2)_mQ$, or phenyl, benzyl, or thiophene substituted with $(CH_2)_mQ$;

n is an integer from 0 to 2;

m is an integer from 0 to 6;

Q is $CO_2R_7$ where R₇ is hydrogen or lower alkyl; and

R₃, R₄, R₅, R₆ are independently hydrogen, hydroxy, nitro, amino, lower alkyl, and lower alkoxy, or a pharmaceutically acceptable salt thereof.

2. The method of claim 1, wherein the compound is selected from 5-methoxy-3-(1-methylethoxy)-benzo[b]thiophene-2-carboxamide;

3-(1-methylethoxy)-benzo[b]thiophene-2-carboxamide;

5-chloro-3-(1-methylethoxy)-benzo[b]thiophene-2-carboxamide;

5-methyl-3-(1-methylethoxy)-benzo[b]thiophene-2-carboxamide;

3-(1-methylethoxy)-5-nitro-benzo[b]thiophene-2-carboxamide;

7-methoxy-3-(1-methylethoxy)-benzo[b]thiophene-2-carboxamide;

3,5-dimethoxy-benzo[b]thiophene 2-carboxamide;

5-methoxy-3-(phenylmethoxy)-benzo[b]thiophene-2-carboxamide;

5-methoxy-3-(phenoxy)-benzo[b]thiophene 2-carboxamide;

5-hydroxy-3-(1-methylethoxy) benzo[b]thiophene-2-carboxamide;

6-methoxy-3-(1-methylethoxy)-benzo[b]thiophene-2-carboxamide;

4-[[[5-methoxy 3-(1-methylethoxy)-benzo[b]thien-2-yl]carbonyl]amino]benzoic acid;

3-[[[5-methoxy-3-(1-methylethoxy)-benzo[b]thien-2-yl]carbonyl]amino]benzoic acid;

ethyl 2-[[[5-methoxy-3-(1-methylethoxy)-benzo[b]thien-2-yl]carbonyl]amino]benzeneacetate;

2-[[[5-methoxy-3-(1-methylethoxy)benzo-[b]thien-2-yl]carbonyl]amino]benzoic acid;

4-[[[5-methoxy-3-(1-methylethoxy)benzo-[b]thien-2-yl]carbonyl]aminomethyl]benzoic acid;

methyl 4-[[[5-methoxy-3-(1-methylethoxy)-benzo[b]thien-2-yl]carbonyl]amino]benzeneacetate;

4-[[[5-methoxy-3-(1-methylethoxy)benzo[b]thien-2-yl]carbonyl]amino]benzeneacetic acid;

methyl 3-[[[5-methoxy-3-(1-methylethoxy)-benzo[b]thien 2-yl]carbonyl]amino]benzeneacetate;

3-[[[5-methoxy-3-(1-methylethoxy)benzo-[b]thien-2-yl]carbonyl]amino]benzeneacetic acid;

methyl 5-[[[5-methoxy-3-(1-methylethoxy)-benzo[b]thien-2-yl]carbonyl]amino]pentanoate;

5-[[[5-methoxy 3-(1-methylethoxy)benzo[b]thien-2-yl]carbonyl]amino]pentanoic acid;

3-[[[5-methoxy-3-(1-methylethoxy)benzo[b]thien-2-yl]carbonyl]amino-2-thiophene-2-carboxamide;

5-methoxy-N-methyl-(3-(1-methylethoxy)-benzo[b]thiophene 2-carboxamide;

N-ethyl-(5-methoxy-3-(1-methylethoxy)benzo-[b]thiophene 2-carboxamide;

5-methoxy-3-(1-methylethoxy) N-phenyl-benzo[b]thiophene-2-carboxamide;

5-methoxy 3-(1-methylethoxy) N-(phenylmethyl)-benzo[b]thiophene-2-carboxamide;

5-methoxy-3-(1-methylethoxy)-benzo[b]thiophene-2-carboxamide-1-oxide;

5-methoxy 3-(1-methylethoxy)-benzo-[b]thiophene-2-carboxamide 1,1'-dioxide;

3-(1,1-dimethylethoxy)-5-methoxybenzo[b]thiophene-2-carboxamide;

6-chloro-3-(1-methylethoxy)benzo[b]thiophene-2-carboxamide;

5-amino-3-(1-methylethoxy)benzo[b]thiophene-2-carboxamide;

methyl 4-[[[5-methoxy-3-(1-methylethoxy)-benzo[b]thien-2-yl]carbonyl]amino]butanoate;

4-[[[5-methoxy-3-(1-methylethoxy)benzo-[b]thien-2-yl]carbonyl]amino]butanoic acid; and 5-methoxy-3-(1-methylethoxy)-N-(1-methylethyl)-benzo [b]thiophene -2-carboxamide.

* * * * *